(12) United States Patent
Farshi et al.

(10) Patent No.: US 8,314,122 B2
(45) Date of Patent: Nov. 20, 2012

(54) USING OF ORGANIC SOLVENTS IN WET GRANULATION OF MOXIFLOXACIN

(75) Inventors: Farhad Farshi, Istanbul (TR); Recep Avci, Istanbul (TR); Fikret Koc, Istanbul (TR); Serdar Soylemez, Istanbul (TR)

(73) Assignee: Abdi Ibrahim Ilac Sanayi Ve Ticaret Anonim Sirketi, Istanbul (TR)

( * ) Notice: Subject to any disclaimer, the term of this patent is extended or adjusted under 35 U.S.C. 154(b) by 0 days.

(21) Appl. No.: 13/122,935

(22) PCT Filed: Oct. 9, 2008

(86) PCT No.: PCT/IB2008/054141
§ 371 (c)(1),
(2), (4) Date: Apr. 6, 2011

(87) PCT Pub. No.: WO2010/041100
PCT Pub. Date: Apr. 15, 2010

(65) Prior Publication Data
US 2011/0198774 A1    Aug. 18, 2011

(51) Int. Cl.
*C07D 471/02* (2006.01)
(52) U.S. Cl. ......... 514/300; 546/113; 264/115; 264/117

(58) Field of Classification Search .................. None
See application file for complete search history.

(56) References Cited

U.S. PATENT DOCUMENTS

| | | |
|---|---|---|
| 5,916,593 A | 6/1999 | De Haan et al. |
| 6,610,327 B1 | 8/2003 | Bosche et al. |
| 2005/0031683 A1 | 2/2005 | Kapoor et al. |
| 2005/0137227 A1 | 6/2005 | Reddy et al. |
| 2006/0252789 A1* | 11/2006 | Biswas et al. ............... 514/300 |

FOREIGN PATENT DOCUMENTS

| | | |
|---|---|---|
| EP | 0350733 | 1/1990 |
| EP | 0780390 | 6/1997 |
| WO | WO 96/09056 | 3/1996 |
| WO | WO 2007/0148137 | 12/2007 |

OTHER PUBLICATIONS

International Search report corresponding to PCT/IB2008/054141 dated Oct. 9, 2008.

* cited by examiner

*Primary Examiner* — Mary F Theisen
(74) *Attorney, Agent, or Firm* — Hershkovitz & Associates LLC; Abraham Hershkovitz

(57) ABSTRACT

This invention encompasses to obtain non-convertible solid pharmaceutical formulations of moxifloxacin anhydrous by using of wet granulation with an organic solvent or mixtures of organic solvents.

3 Claims, 3 Drawing Sheets

[Fig. 1]
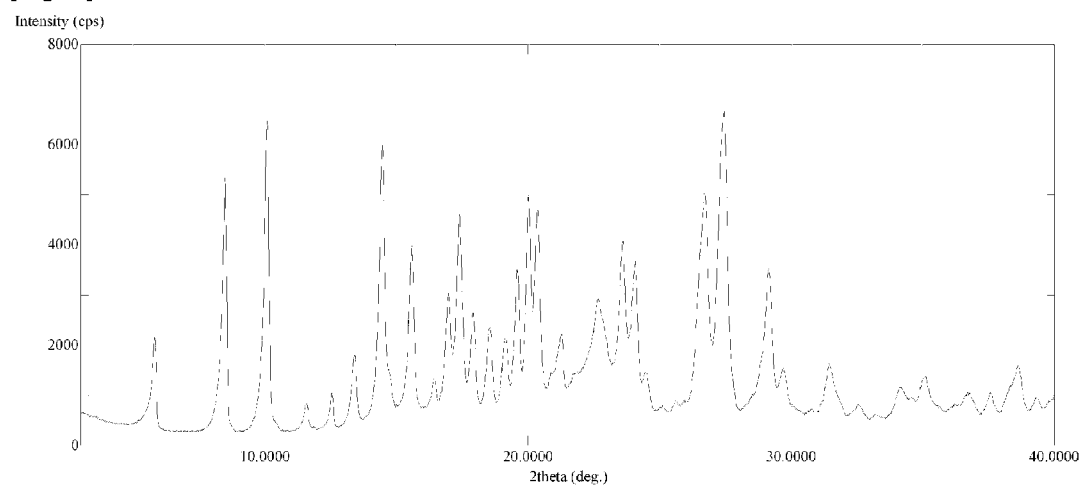
[Fig. 2]
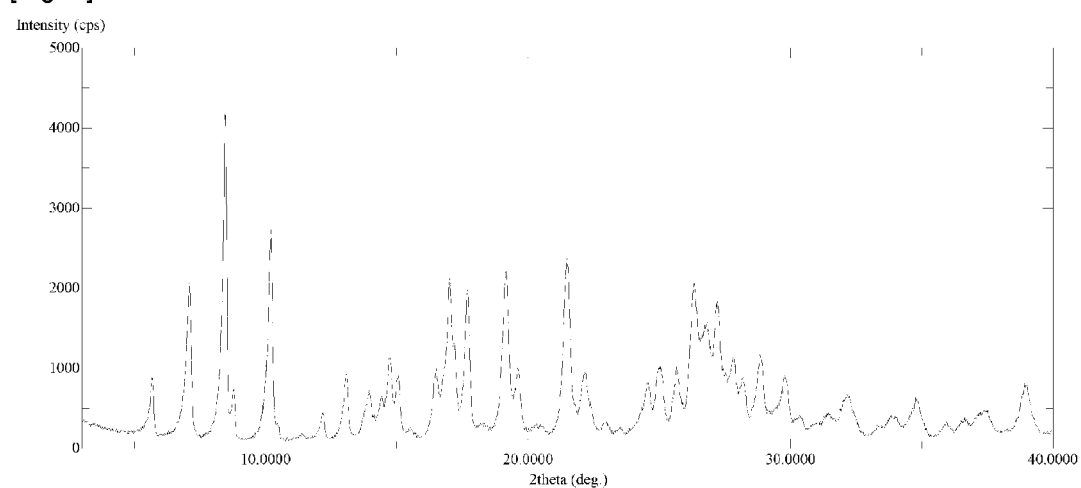
[Fig. 3]
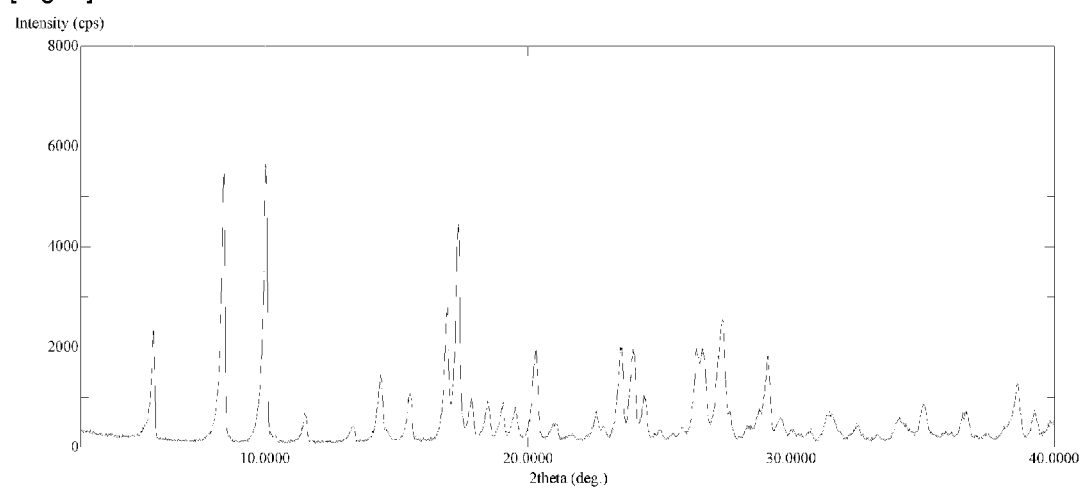

[Fig. 4]
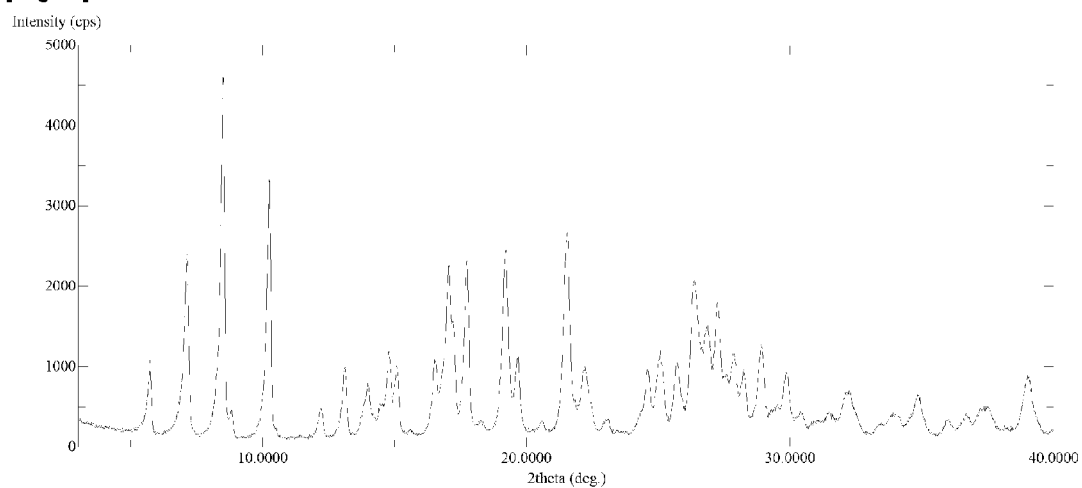
[Fig. 5]
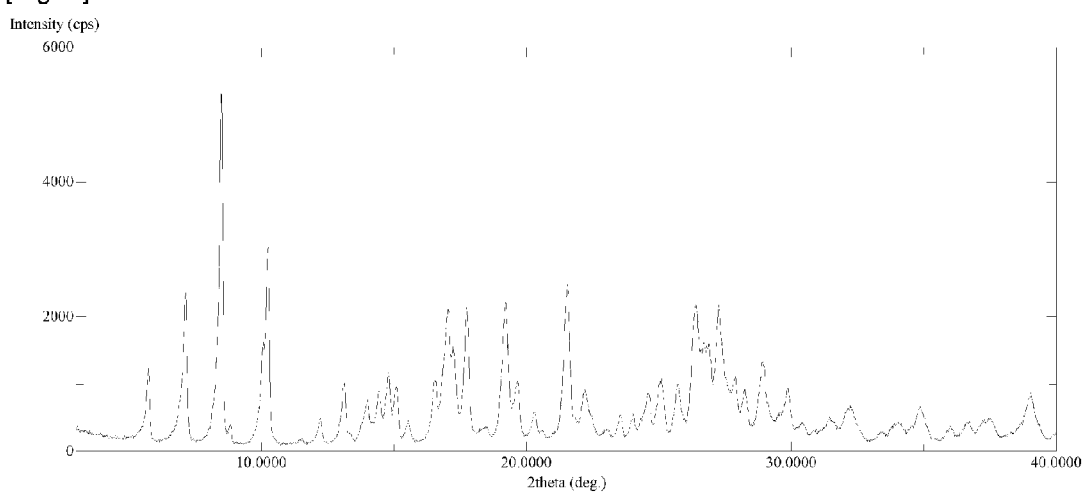
[Fig. 6]
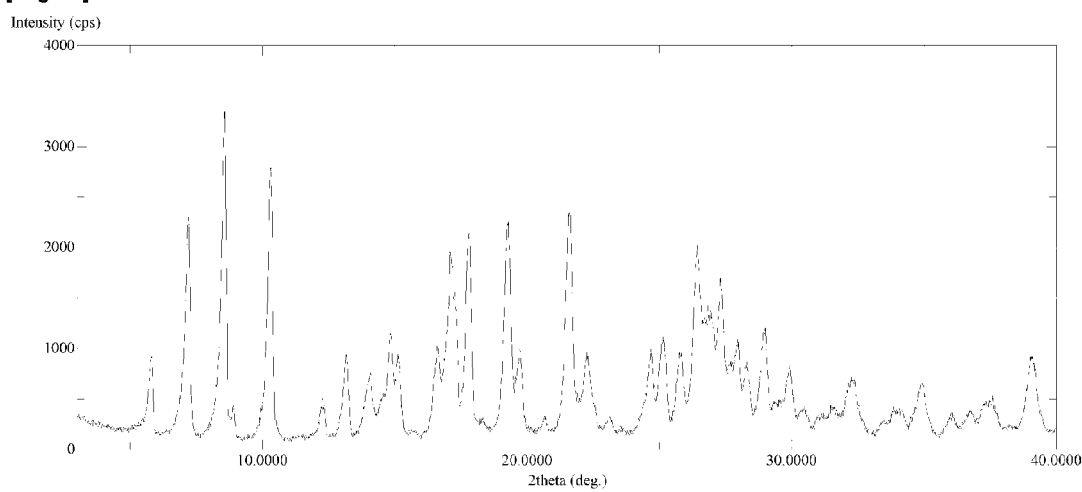

[Fig. 7]
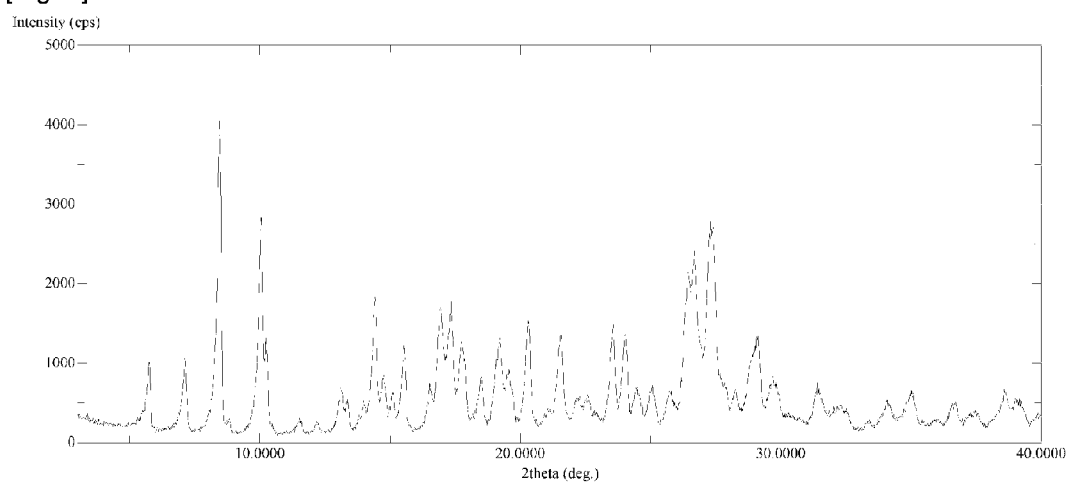

USING OF ORGANIC SOLVENTS IN WET GRANULATION OF MOXIFLOXACIN

EP 0350733 describes moxifloxacin as antiinfective agent.

U.S. Pat. No. 6,610,327 (TR0101310) discloses a pharmaceutical composition comprising moxifloxacin or a salt and/or hydrate, at least one dry binder, at least one disintegrant, at least one lubricant and lactose from 2.5% to 25%. The subject matter of the patent is to provide a pharmaceutical formulation which can be used to prepare tablets having sufficient hardness or breaking load, at the same time have excellent release properties. That aim is achieved through using of a certain amount of lactose in the range of from 2.5% to 25% by weight.

EP 0 780 390 (TR0970481) claims crystalline forms of moxifloxacin hydrochloride monohydrate. Avalox® includes moxifloxacin hydrochloride monohydrate as disclosed in the patent of EP 0 780 390 and X-ray powder diffractogram could be seen (FIG. 1).

Anhydrous moxifloxacin hydrochloride is suitable to obtain soluble pharmaceutical composition rather than moxifloxacin hydrochloride monohydrate. The presence of water in crystals is more prone to degradation and thus anhydrous moxifloxacin hydrochloride is preferred.

Using of anhydrous moxifloxacin hydrochloride, of which X-ray powder diffractogram could be seen (FIG. 2), in pharmaceutical formulations provides eligible stability therefore preferred rather than moxifloxacin hydrochloride monohydrate. However in granulation phase if wetting agent is water instead of organic solvent or mixtures of organic solvents, anhydrous moxifloxacin hydrochloride is instantly converted to moxifloxacin hydrochloride monohydrate. It is not desired and it should be prevented.

The aim of this invention is to obtain non-convertible solid pharmaceutical formulations of anhydrous moxifloxacin by using of wet granulation with an organic solvent or mixtures of organic solvents. Under specific conditions, it is desired that anhydrous moxifloxacin hydrochloride should permanently have properties of its own form without converting to form mentioned in EP 0 780 390 after wet granulation and becoming dosage form. Anhydrous moxifloxacin hydrochloride, other than form of EP 0 780 390, should permanently maintain its properties in the course of preparation of formulation and during storage. Therefore it should be obtained that non-convertible formulations and methods of preparation. Consequently, technical problem is converting to moxifloxacin monohydrate and panacea is to obstacle of converting through using of an organic solvent or mixtures of organic solvents in the wet granulation.

According to present invention pharmaceutical composition comprises anhydrous moxifloxacin hydrochloride, microcrystalline cellulose, polyvinylpyrrolidone, mannitol, croscarmellose sodium, magnesium stearate and other suitable excipients. Mentioned excipients are not limited and could be contemplated with another excipients which have identical or same characteristics of said excipients. Moxifloxacin term is used as broadest sense and encompasses all of the salts, bases and other derivatives and forms.

A wet granulation method with an organic solvent or mixtures of organic solvents is describe herein in which the organic solvent or mixtures of organic solvents are selected from isopropyl alcohol (IPA), acetone, ethanol, dichloromethane and mixtures thereof. Organic solvent or mixtures of organic solvents are preferred since using of water in wet granulation entails conversion from anhydrous moxifloxacin hydrochloride to moxifloxacin hydrochloride monohydrate (FIG. 3). It is not desired to be converted and thence If conversion is not desired, then granulation should not be performed with water or water mixtures. Anhydrous moxifloxacin hydrochloride should not be exposed to water in the preparation stage. The organic solvent is selected from isopropyl alcohol (IPA), acetone, ethanol, dichloromethane or mixtures thereof in the wet granulation method so as to obtain non-convertible formulations (respectively FIG. 4, FIG. 5, FIG. 6, FIG. 7).

EXAMPLE 1

POVIDONE K-30 (polyvinylpyrrolidone) is added to isopropyl alcohol and mixed until the POVIDONE K-30 (polyvinylpyrrolidone) is completely dissolved (Step 1). Moxifloxacin Hydrochloride and Microcrystalline Cellulose are transferred to a granulator and mixed (Step 2). The granulation solution from step 1 is added to the powder mixtures from step 2 and mixed. Wet granules are taken from the granulator to the oven and dried. The granules are sieved. MANNITOL SD 200 (mannitol) and croscarmellose sodium are transferred to the mixtures in the container and mixed. Magnesium stearate is sieved and added to the mixtures in the container and sieved. The blend is tabletted using appropriate punches according to the specifications. X-ray powder diffractogram of the treatment with isopropyl alcohol is shown in FIG. 4. As seen in FIG. 4, there is no conversion. If the same granulation is iterated with acetone (FIG. 5), ethanol (FIG. 6) or dichloromethane (FIG. 7) instead of isopropyl alcohol, there is no conversion to moxifloxacin hydrochloride monohydrate.

The invention claimed is:

1. A wet granulation method of anhydrous moxifloxacin or its salts wherein the method utilizes a wetting agent and the wetting agent is selected from group of isopropyl alcohol, acetone, ethanol, dichloromethane or mixtures thereof.

2. The method of claim 1, wherein the wet granulation method comprises:
   (a) adding polyvinylpyrrolidone to isopropyl alcohol and mixing until the polyvinylpyrrolidone is completely dissolved;
   (b) transferring and mixing Anhydrous Moxifloxacin Hydrochloride and Microcrystalline Cellulose in a granulator;
   (c) adding and mixing a granulation solution from step (a) to powder mixtures from step (b);
   (d) taking wet granules from the granulator to an oven and drying and sieving the granules;
   (e) transferring and mixing mannitol and Croscarmellose Sodium to the mixture in a container;
   (f) sieving and adding Magnesium Stearate to the mixtures in the container to produce a blend; and
   (g) producing tablets from the blend by utilizing punches.

3. The method of claim 1, wherein the anhydrous moxifloxacin salt is hydrochloride.

* * * * *